US00RE39626E

(19) United States
(12) Reissued Patent
Tihon

(10) Patent Number: US RE39,626 E
(45) Date of Reissued Patent: May 15, 2007

(54) FEMALE INCONTINENCE PREVENTION DEVICE

(75) Inventor: Claude Tihon, Eden Prairie, MN (US)

(73) Assignee: ConSert, LLC, Minnetonka, MN (US)

(21) Appl. No.: 10/621,243

(22) Filed: Jul. 15, 2003

Related U.S. Patent Documents

Reissue of:
(64) Patent No.: 6,311,689
Issued: Nov. 6, 2001
Appl. No.: 09/522,486
Filed: Mar. 10, 2000

(51) Int. Cl.
*A61F 5/48* (2006.01)

(52) U.S. Cl. ..... 128/885; 128/DIG. 25; 600/29

(58) Field of Classification Search ..... 128/885, 128/DIG. 25; 600/29–31
See application file for complete search history.

(56) References Cited

U.S. PATENT DOCUMENTS 365,969 A * 7/1887 Collins ..... 604/105
3,372,695 A * 3/1968 Beliveau et al. ..... 600/29
4,738,667 A * 4/1988 Galloway ..... 604/281
5,176,664 A * 1/1993 Weisman ..... 604/317
5,352,182 A * 10/1994 Kalb et al. ..... 600/30
5,562,622 A * 10/1996 Tihon ..... 604/105
5,738,654 A * 4/1998 Tihon ..... 604/105
5,887,593 A * 3/1999 Levius ..... 128/885

FOREIGN PATENT DOCUMENTS

WO WO 97/32542 * 9/1997

* cited by examiner

*Primary Examiner*—Michael A. Brown
(74) *Attorney, Agent, or Firm*—Thomas J. Nikolai; Nikolai & Mersereau, P.A.

(57) ABSTRACT

The disclosure provides an incontinence prevention device provided with a loop type retention structure. The retention structure is in the form of a closed loop attached to the distal end of a shaft. The shaft is configured to function as an incontinence prevention device. The retention structure projecting laterally from and configured non-concentrically along the longitudinal axis of the shaft retains the incontinence prevention device within the patient. The retention structure may additionally include a protuberance extending therefrom. There is further provided a method for using the urethral catheter.

14 Claims, 5 Drawing Sheets

FEMALE INCONTINENCE PREVENTION DEVICE

Matter enclosed in heavy brackets [ ] appears in the original patent but forms no part of this reissue specification; matter printed in italics indicates the additions made by reissue.

FIELD OF INVENTION

The present invention relates generally to incontinence prevention devices, and more particularly to an incontinence prevention devices having a non-concentric retention structures.

BACKGROUND OF INVENTION

Many adults suffer urinary incontinence although urinary incontinence is more common in women than in men. The increased frequency in women is due primarily to the laxity of the bladder support structures resulting from pregnancy and aging. Surgical correction is possible in some cases, but surgery is invasive, costly and dangerous. Urethral incontinence prevention devices, such as for example catheters, plugs and other similar devices, in most cases offer a better solution but can be cumbersome to use, can be expelled during bowel movements, and are typically relatively expensive to manufacture.

There are a wide variety of incontinence prevention devices available, including: catheters that have lumen for urine to flow through; valved catheters; plugs that prevent the flow of urine until the plug is removed; and cylindrical supports against which the spinchter seals the urethra to prevent the flow of urine. Foley catheters are one type of commonly used catheter. Foley catheters are essentially elongated tubes. They are placed in the urethra to drain urine through the central lumen. An inflatable balloon is included near the distal end of the tube serves as a retention structure. When inflated, the balloon holds the catheter in place. The proximal end of a Foley catheter typically has two ports: a drainage port to drain urine from the bladder and a balloon inflation port to inflate and deflate the balloon. The drainage port creates a permanent opening between the bladder and outside environment. Because the bladder is continuously emptied, the bladder's dome continuously rests on the tip of the catheter above the retention balloon causing compression, irritation and erosion of tissue as well as other tissue problems. Therefore, a need exists for a retention structure that does not protrude into the bladder such that it contacts the bladder's dome.

Plugs totally block the flow of urine. Therefore, the plugs typically require removal for the user to urinate. After removal, the old plug is not sterile and a new sterile plug must inserted into the urethra Plugs' retention structures are typically cumbersome to operate and traumatic to the tissue. Thus, improper use can lead to irritation and infection from tissue traumatization. Further, the retention devices on the plugs are typically fluid filled and therefore relatively complex to manufacture. Therefore, a need exists for an incontinence prevention device that provides an atraumatic and simple means for insertion and removal and further reduces manufacturing costs.

Further, some urethral incontinence devices include open loop or pigtail type retention structures. These devices may be expelled when a user tenses the abdomen, such as when a user bears down during a bowel movement, because of a phenomenon called bladder neck drop often associated with incontinent female patients. With bladder neck drop, the bladder neck extends downward to encompass at least a portion of the urethra. The open loop type retention structures are thought to drop into the downward extension and thereafter could be entrapped in the urethra rendering it quasi-rectilinear as the bladder neck resumes its original shape. The improperly positioned device no longer functions properly and the quasi-rectilinear bladder retention structure can no longer maintain the device at its proper location permitting the user to later expel the device. Therefore, a need exists for an incontinence prevention device having a retention structure that maintains its appropriate position within the bladder neck regardless the physical forces acting on it, and can recover after momentary bladder neck drop.

In addition, typical incontinence prevention devices require, at least to some extent, that a proximal end extend from the urethral meatus. The proximal ends tend to scatter urine droplets during urination. The scattering of urine is inconvenient and unsanitary. Therefore, a need exists for a catheter that permits a directed stream of urine.

The present invention meet these needs and provides additional improvements and advantages that will be recognized by those skilled in the art upon review of the following description and figures.

SUMMARY OF THE INVENTION

The present invention further provides an incontinence prevention device that is simple and inexpensive to construct and easy to use. The incontinence prevention device of the present invention includes a shaft and a retention structure. The retention structure is configured as a closed loop non-concentrically disposed about a longitudinal axis of the shaft. The retention structure's closed loop tends to maintain the incontinence prevention device within the bladder neck. The retention structure's non-concentrically orientation accounts for the bladder's asymmetry. The retention structure may further include a protuberance projecting from the retention structure. The protuberance may project from a midpoint of the closed loop. The shaft may further include a lumen configured to receive a stylet. The lumen is typically coextensive with the shaft and substantially coextensive with the retention structure. In addition, the lumen may be coextensive with the protuberance. The device may also include a hydrogel coating disposed on its outer surface. The shaft may include an orientation marking at its proximal end. The proximal end of the shaft may also have a beveled edge to prevent the spraying of urine during urination. A segment of the retention structure may additionally define a cavity to receive another portion of the retention structure to further reduce the diameter for insertion. For insertion, the retention structure is rendered substantially rectilinear. A stylet may be provided to insert into a lumen in the device to render the retention structure substantially rectilinear. Once rectilinear, the device is inserted into the urethra so that the retention structure is placed within the bladder. Once in the bladder, the retention structure is reformed into a loop. The retention structure is then positioned adjacent the neck of the bladder with the non-concentrically disposed retention structure in a predetermined orientation.

DETAILED DESCRIPTION OF THE INVENTION

Figure 1:
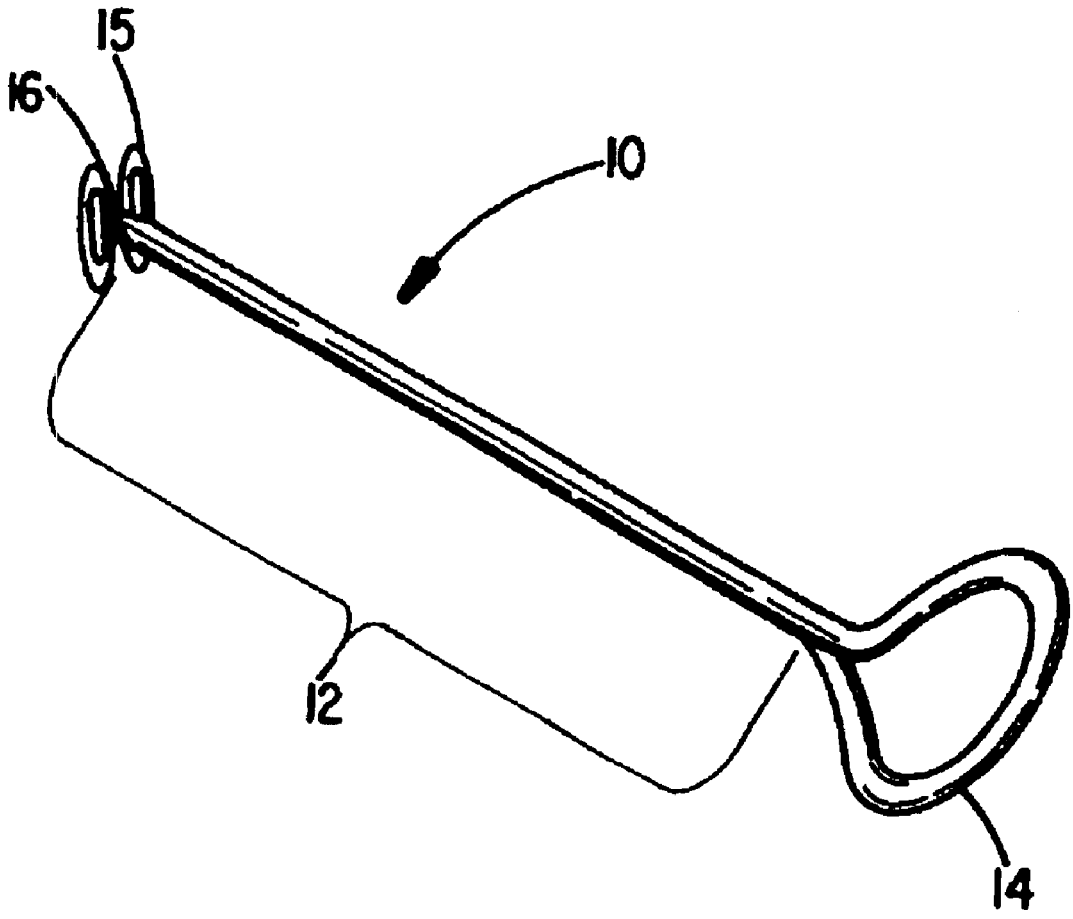
FIG. 1 illustrates a perspective view of a urethral catheter showing a first embodiment of the retention mechanism.

The present invention is applicable to a variety of devices that are maintained in the urethra. The invention is described in the context of an incontinence device for a woman's urethra for exemplary purposes. The appended claims are not intended to be limited to any specific example or embodiment described in this specification. It will be understood by those skilled in the art that the present invention may be used in related medical applications including but not limited to incontinence prevention devices, obstruction relief devices, drainage devices; or other similar devices which require retention in a lumen. Further, in the drawings described below, the reference numerals are generally repeated where identical elements appear in more than one figure.

FIG. 1 illustrates an embodiment of an incontinence prevention device 10 in accordance with the present invention. Device 10 includes a shaft 12, a retention structure 14 and a proximal retention structure 15. Device 10 may further includes a lumen 18, shown in FIG. 2. Device 10 is typically circular in cross-section although other shapes such as oval that allow the sphincter to sealably contract against the catheter's outer surface may also be used. Device 10 is typically composed of a flexible biocompatible material such as silicone, silastic, polyurethane, polyethylene, polyimide, PTFE, ETFE, or other materials or combinations of materials known to those skilled in the art. Typically, the material used has a durometer shore hardness of between about 30 and 95 shore A. In addition, device 10 may be coated with a lubricious material, such as a bydrogel, to allow for easier insertion and reduced irritation.

Shaft 12 is typically configured as a semi-rigid region of device 10 typically having a shape suitable for placement in the urethra Shaft 12 is further configured to have sufficient rigidity for sphincter muscles to contract against it so as to substantially stop the flow of urine from a user's bladder. Shaft 12 may also include an orientation marking 38, shown in FIGS. 5B and 5C and discussed below. The orientation making may either be visible, for example a line or dot, or tactile, for example a crevice or dimple. Shaft 12 typically has a diameter of around 8 French to correspond with an appropriate size for insertion in an adult female's urethra. The device can be made with various other diameters ranging from between about 5 to 16 French to enable the proper sizing to accommodate the range of urethral sizes. The shaft typically has a length of between about 3.5 to 4.5 centimeters enabling the proper sizing of the catheter's length for most women's urethra. The proximal end includes a proximal retention structure 15. Proximal retention structure 15 generally functions to prevent the incontinence prevention device from moving up into the urethra and provides a means for gripping the incontinence prevention device during removal. Proximal retention structure 15 is typically configured to conform to the vestibule proximate the urethral opening. The proximal end of the shaft may also include a beveled edge 16. Beveled edge 16 tends to prevent the spraying of urine during urination. In addition, the proximal end typically includes a structure for preventing the incontinence prevention device from tracking up the urethra.

Figure 2:
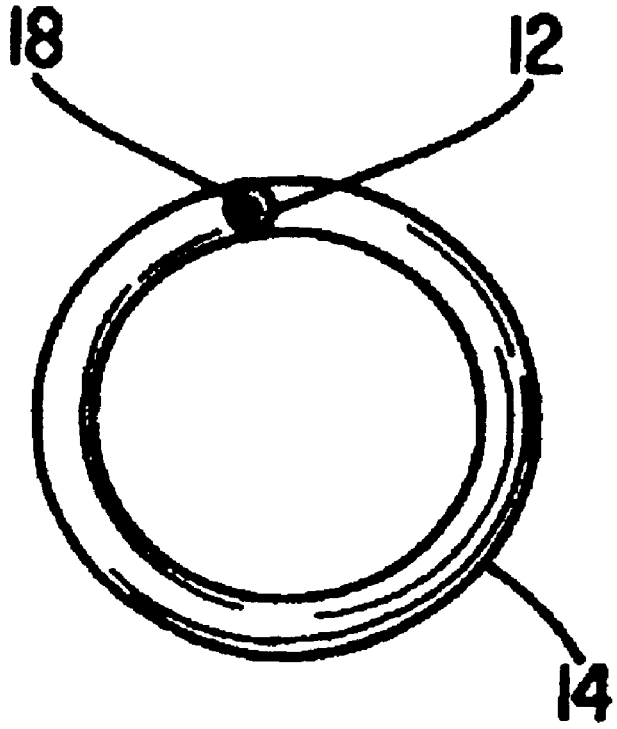
FIG. 2 illustrates a left end view of the urethral catheter of FIG. 1.

Retention structure 14 comprises a closed loop at the distal end of the shaft non-concentrically disposed about shaft 12. Retention structure 14 may be integral with shaft 12 or a separate element that is secured to shaft 12. FIG. 2 shows a proximal end view of device 10 of FIG. 1 illustrating an embodiment of the non-concentric relationship of shaft 12 to retention structure 14. Retention structure 14 projects in a general lateral direction from the shaft and is typically non-concentrically disposed about shaft 12. Retention structure 14 is typically shaped to be received at the base of the urinary bladder and above the bladder's neck. Retention structure 14 maintains the incontinence prevention device in position as the bladder neck rises and drops with patient activity. The retention structure is thought to be maintained within the bladder as a moist watermelon seed is ejected when squeezed between one's thumb and forefinger. Thus, when the retention structure slips below the neck and into the urethra, there is a tendency for the retention structure to be forced back into the bladder as the bladder neck and/or urethra resume their original orientation. Typically, a device having a retention structure in accordance with the present invention is capable of maintaining the catheter's position regardless of the forces typically encountered. However, the device may be removed by simply pulling on the proximal end with sufficient force to collapse the retention structure.

The retention structure may be substantially circular, as shown in FIG. 2, or may have various shapes appropriate for holding device 10 within the urethra that will be recognized by those skilled in the art. The retention structure is configured to be collapsible for insertion through the urethra and to regain its shape after insertion once in the bladder. After insertion, the retention structure has sufficient rigidity to hold the retention structure within the urinary bladder. To retain its shape, the retention structure may include an internal wire or be composed of a material with sufficient memory to regain the loop configuration.

In addition, FIG. 2 shows lumen 18 extending through the proximal end of shaft 12.

Figure 3:
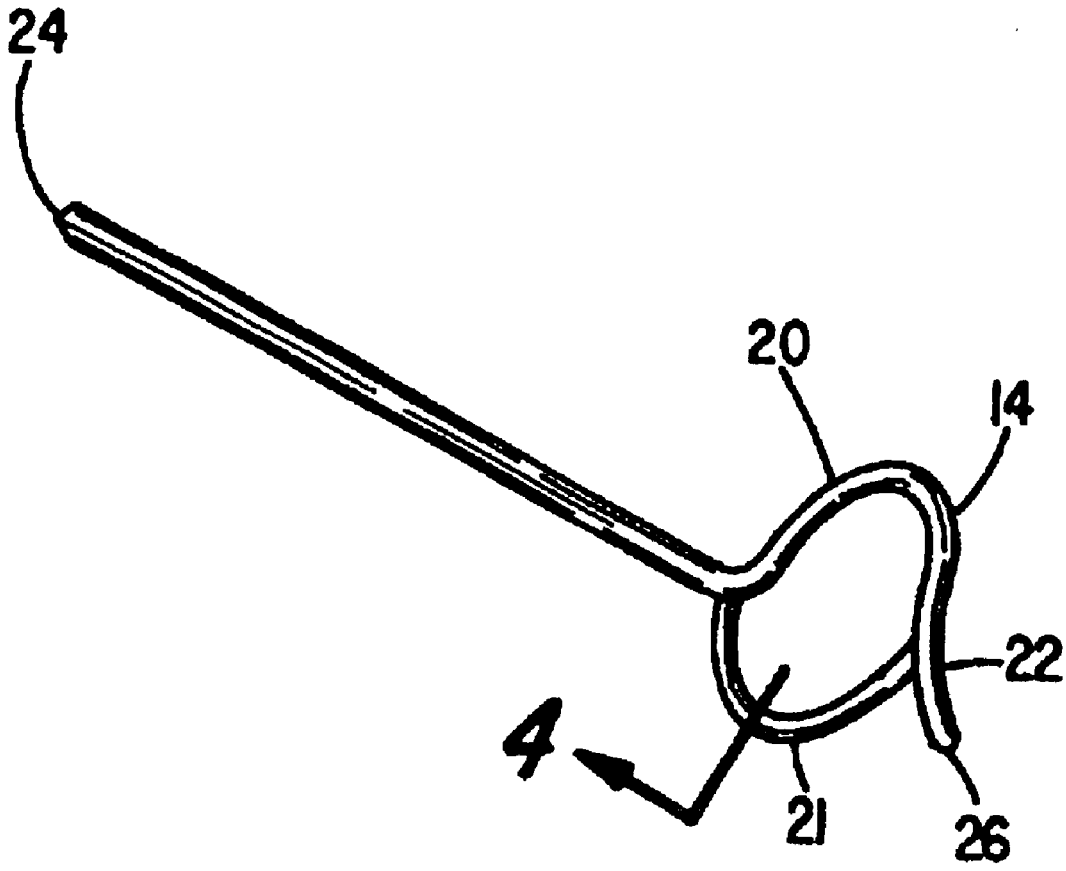
FIG. 3 illustrates a perspective view of a urethral catheter showing a second embodiment of the retention mechanism.

FIG. 3 shows an alternative embodiment of the retention structure. In the embodiment of FIG. 3, retention structure 14 includes a protuberance 22 projecting from the loop. In addition and as discussed in more detail below, a segment 21 may be attached to shaft 12 to form the loop and to provide protuberance 22. Protuberance 22 forms a smaller leading tip for easier insertion and helps to maintain the incontinence prevention device on a stylet during insertion. To facilitate this, protuberance 22 typically includes a lumen that is coextensive with lumen 18 of shaft 12. That is, lumen 18 extends from a proximal end incontinence prevention device 10 to a distal end 26. Typically, the lumen does not extend through distal end 26 but only to a point immediately proximal to distal end 26. This configuration prevents the flow of urine through the lumen. Alternatively, the incontinence prevention device may have the lumen extending through distal end 26 to allow fluid flow through the lumen as required for some applications. When the retention structure includes a portion of the shaft, a segment 21 is typically provided to complete the loop comprising retention structure 15. Segment 21 is typically attached at one end to a first location proximate to distal end 26 of shaft 12 and, at the segment's other end, to a second location along the shaft closer to the shaft's proximal end so as to form a loop. Typically, the length of segment 21 and the positions for its attachment are selected so as to permit the loop to assume an appropriate configuration for insertion into the urethra and subsequent reformation into a loop when in the bladder.

Figure 4:
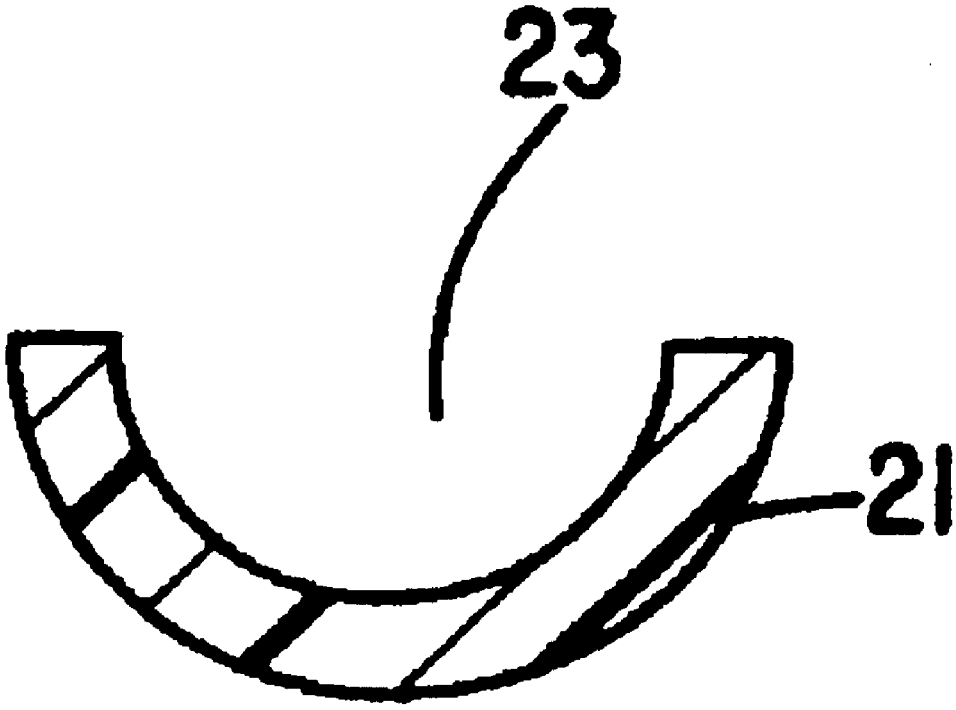

Shaft 12 and segment 21 may be configured to appear as a single unit for insertion. That is, when you straighten out the loop the two elements have the appearance of being one element. One such configuration may include configuring segment 21 as a horseshoe defining a cavity 23, as shown in cross-section in FIG. 4. Shaft 12 is then shaped to be received within cavity 23. When the loop is collapsed, cavity 23 receives shaft 12 and the retention structure appears as one element instead of a separate segment 21 and shaft 12. The actual circumference of the retention structure is therefore reduced making it physically easier to insertion and less traumatic on the patient. In addition, the thinner appearance would tend to be less intimidating to a patient.

The shaft and retention structure may be composed of a uniform material or may be composed of layers of material to confer the desired characteristics. When layered, the structure may include, for example, an inner layer of polyurethane surrounded by an outer layer of silicone or other combinations that confer desired characteristics. For example, the layered structures may be formed by inserting a polyurethane tube inside a silicone sleeve. The fit between the polyurethane tube and silicone sleeve is such that their contact minimizes slippage between the two. To develop sufficient contact, the silicone sleeve is typically soaked in a suitable solvent to swell the sleeve. The polyurethane tube is then inserted into the sleeve. As the solvent evaporates, the silicone sleeve contracts against the polyurethane tube. Typically, only the shaft is provided with such a silicon sleeve.

Using the above method of manufacture, the polyurethane tube holds the structure together while the silicone provides an appropriate surface for the sphincter to contract against. In addition, the retention structure may be integral with the shaft or formed independent of the shaft. When integral, device 10 may be formed from a single tube having its distal end wrapped around and secured to the tube to separately define the shaft and the retention structure. When formed independently, the retention structure may have a different shape and physical characteristics than the shaft.

Figure 5A:
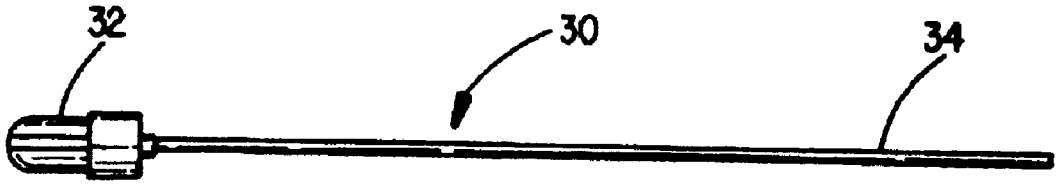
FIG. 5A illustrates a side view of a stylet.
Figure 5B:
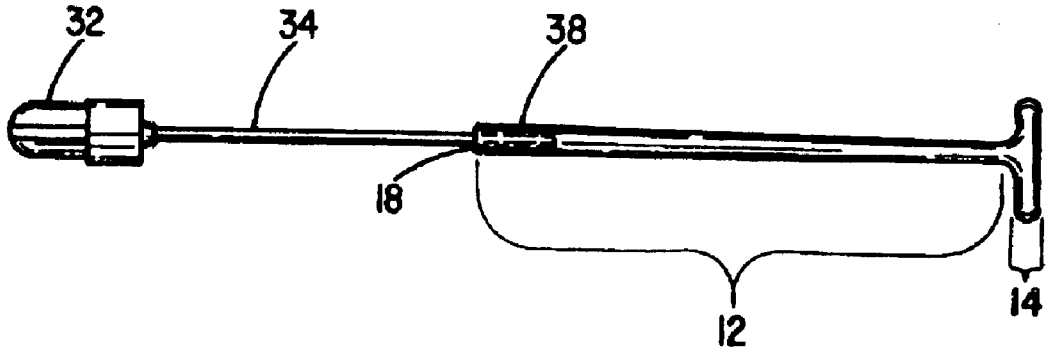
FIG. 5B illustrates a side view urethral catheter of FIG. 1 with a stylet partially inserted into the urethra measuring device.
Figure 5C:
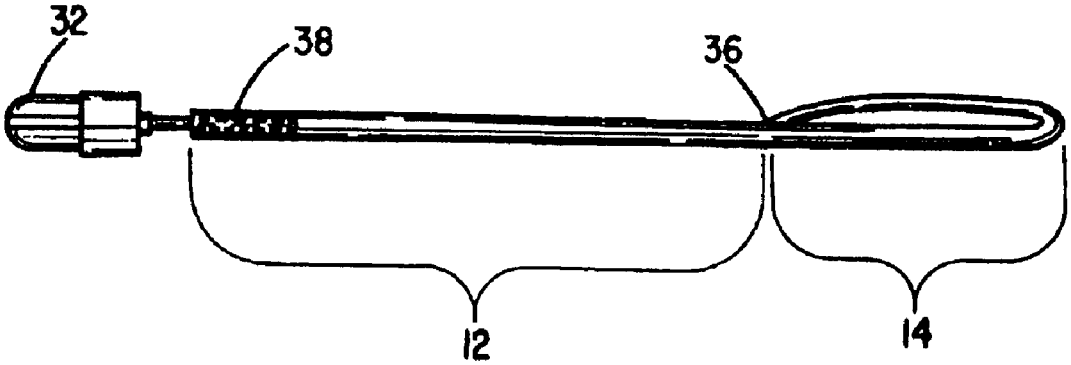
FIG. 5C illustrates a side view urethral catheter of FIG. 1 with a stylet fully inserted into the urethra measuring device.

The method of using a incontinence prevention device in accordance with the present invention is best understood with reference to FIGS. 5A, 5B and 5C. The figures illustrate a method of linearizing a device 10, as shown in FIG. 1, for insertion into the urethra. FIG. 5A shows an insertion tool 30 having a handle 32 attached to a stylet 34. Handle 32 is not required but is typically provided for better control of the catheter during insertion. Stylet 34 is composed of a material, typically a metal wire, having sufficient rigidity to facilitate the insertion of the catheter into the urethra. Stylet 34 is typically sized to fit within lumen 18 of device 10. In use, stylet 34 is inserted into shaft 12 through lumen 18 at the shaft's distal end, as shown in FIG. 5B. Stylet 34 is advanced into shaft 12 through lumen 18. Once the stylet's distal end reaches retention structure 14, retention structure 14 assumes a conformation allowing insertion through the urethra, as shown in FIG. 5C, due to forces conferred by stylet 34. At this point, lubrication is typically applied to device 10. If the device is hydrogel coated, the device is lubricated simply by moistening the material. Alternatively, a water-soluble lubricant, like K-Y Jelly, or other suitable lubricant may be applied to the catheter's surface. In the embodiment shown, stylet 34 is typically advanced until retention structure 14 collapses in on itself due to the rigidity of the stylet and the tension exerted between the distal tip of stylet 30 and the point 36 where the loop attaches to shaft 12. Thus, insertion of the stylet renders urethral catheter 14 substantially rectilinear so as to allow insertion into a urethra. Retention structure 14 is then inserted into the urethra. Once retention structure 14 of the incontinence prevention device 10 is positioned within the urinary bladder, the stylet is removed allowing retention structure 14 to resume its original configuration. The proximal end of device 10 is then manipulated, if necessary, to properly orient non-concentrically configured retention structure 14 adjacent to the bladder neck within the patient. The orientation of retention structure 14 may be reflected by reference to orientation marking 38 on shaft 12. Thus, for example, when orientation marking 38 is oriented ventrally, retention structure 14 is properly oriented within the patient's bladder.

What is claimed is:

1. An incontinence prevention device comprising:

(a) a flexible shaft member sized to fit within the urethra of a female; and (b) a retention structure formed on a distal end of the flexible shaft, the retention structure forming a perimeter of a closed loop defining a plane that is generally [perpendicular] *lateral* to a longitudinal axis of the flexible shaft when the retention structure is unrestrained, said longitudinal axis being offset from a center of the closed loop so as to pass through the perimeter of the closed loop.

2. An apparatus, as in claim 1, further comprising a lumen configured to receive a stylet, wherein the lumen is coextensive with the shaft and substantially coextensive with the retention structure.

3. An apparatus, as in claim 1, further comprising a hydrogel coating disposed on an outer surface of the catheter.

4. An apparatus, as in claim 1, wherein the shaft includes an orientation marking at a proximal end of the shaft.

5. An apparatus, as in claim 1, wherein a proximal end of the shaft includes a beveled edge.

6. An apparatus, as in claim 1, wherein the retention structure further includes a protuberance projecting from the retention structure.

7. An apparatus, as in claim 6, wherein the protuberance projects from a midpoint of the closed loop.

8. An apparatus, as in claim 6, further comprising a lumen coextensive with the shaft and protuberance configured to receive a stylet.

9. An apparatus, as in claim 8, wherein the lumen extends through a distal end of the protuberance.

10. An apparatus, as in claim 8, wherein the lumen extends to a point proximal to a distal end of the protuberance.

11. An apparatus, as in claim 6, wherein a segment of the retention structure defines a cavity to receive a portion of the retention structure.

12. A method treating incontinence, comprising:

providing an apparatus including a shaft and a retention structure, wherein the retention structure forms a perimeter of a closed loop defining a plane that is generally [perpendicular] *lateral* to a longitudinal axis of the shaft and the longitudinal axis of the shaft is offset from a center of the closed loop and passes through the perimeter of the closed loop when the retention structure is unrestrained;

rendering the retention structure substantially rectilinear;

inserting the rectilinear retention structure through a urethra into a bladder;

reforming the retention structure into the closed loop; and positioning the retention structure adjacent the neck of the bladder with the retention structure in a predetermined orientation.

13. The method, as in claim 12, wherein the apparatus further comprises a lumen configured to receive a stylet, wherein the lumen is coextensive with the shaft and substantially coextensive with the retention structure.

14. The method, as in claim 13, (12, further comprising providing a stylet and) wherein the stylet is inserted into the lumen in the apparatus to render the retention structure substantially rectilinear.

* * * * *